(12) United States Patent
Grawe et al.

(10) Patent No.: US 7,799,770 B2
(45) Date of Patent: Sep. 21, 2010

(54) SOLID BODY FORMS OF MESOPROGESTIN 11β-{4E-(HYDROXYIMINOMETHYL)-PHENYL}-17α METHOXYMETHYL-17β-METHOXY-ESTRA-4,9-DIEN-3-ONE

(75) Inventors: Detlef Grawe, Kleinromstedt (DE); Peter Hosel, Jena (DE); Uwe Muller, Jena (DE); Gabriele Winter, Schonfliess (DE)

(73) Assignee: Bayer Schering Pharma AG, Berlin (DE)

( * ) Notice: Subject to any disclaimer, the term of this patent is extended or adjusted under 35 U.S.C. 154(b) by 1884 days.

(21) Appl. No.: 10/296,463

(22) PCT Filed: May 9, 2001

(86) PCT No.: PCT/EP01/05237

§ 371 (c)(1), (2), (4) Date: Jul. 24, 2003

(87) PCT Pub. No.: WO01/90137

PCT Pub. Date: Nov. 29, 2001

(65) Prior Publication Data

US 2004/0006241 A1    Jan. 8, 2004

(30) Foreign Application Priority Data

May 23, 2000 (EP) ................................. 00110887

(51) Int. Cl.
*A61K 31/56* (2006.01)
*C07J 1/00* (2006.01)
(52) U.S. Cl. .................. 514/179; 514/843; 552/648
(58) Field of Classification Search ................ 514/179; 552/648
See application file for complete search history.

(56) References Cited

U.S. PATENT DOCUMENTS 5,693,628 A * 12/1997 Schubert et al. ............. 514/179

FOREIGN PATENT DOCUMENTS

| EP | 0 648 778 | 4/1995 |
| WO | WO 97 32890 | 9/1997 |
| WO | WO 97/32890 | * 9/1997 |

OTHER PUBLICATIONS

English translation of WO 97/32890 filed Sep. 1997.*

* cited by examiner

*Primary Examiner*—Barbara P Badio
(74) *Attorney, Agent, or Firm*—Millen, White, Zelano, Branigan, P.C.

(57) ABSTRACT

The invention relates to novel solid body forms of mesoprogestin 11β-[4E-(hydroxyiminomethyl)-phenyl]-17α-methoxymethyl-17β-methoxy-estra-4,9-dien-3-one (oxime J 867), particularly a highly pure and stable amorphous or highly crystalline form (ansolvate/anhydrate) of compound J 867. The invention also relates to methods for producing said novel solid body forms and to the use thereof in pharmaceutical compositions. The novel solid body forms are characterized by exhibiting a high degree of stability. The solid body forms of oxime J 867 can, in particular, be used in the area of fertility control and in hormone replacement therapy.

14 Claims, 7 Drawing Sheets

X-Ray-powder diffractogram of the isopropanol solvate (14% isopropanol) of 11β-[4E-(hydroxyiminomethyl)phenyl]-17α-methoxymethyl-17β-methoxy-estra-4,9-dien-3-one (EP-A-0 648 778)

Solubility of highly crystalline (──■──) 11β-[4E-(hydroxyiminomethyl)phenyl]-17α-methoxy-methyl-17β-methoxy-estra-4,9-dien-3-one ansolvate or amorphous (──◆──) 11β-[4E-(hydroxyiminomethyl)phenyl]-17α-methoxymethyl-17β-methoxy-estra-4,9-dien-3-one in water with and without surfactant

SOLID BODY FORMS OF MESOPROGESTIN 11β-{4E-(HYDROXYIMINOMETHYL)-PHENYL}-17α METHOXYMETHYL-17β-METHOXY-ESTRA-4,9-DIEN-3-ONE

This invention relates to new forms of solids of the mesoprogestin 11β-[4E-(hydroxyiminomethyl)phenyl]-17α-methoxymethyl-17β-methoxy-estra-4,9-dien-3-one (oxime J 867), especially a highly pure and stable amorphous or highly crystalline form (ansolvate/anhydrate) of the compound J 867, process for their production as well as their use in pharmaceutical compositions.

11β-[4E-(Hydroxyiminomethyl)phenyl]-17α-methoxymethyl-17β-methoxy-estra-4,9-dien-3-one is known, for example, from EP-A-0 648 778 or DE-A-43 32 283. The form that is obtained there after recrystallization from methylene chloride/isopropanol melts at 113° C. The crystal form that is described is an isopropanol solvate with 14% isopropanol (see XRPD: Table 2/FIG. 4d). A characteristic feature of the oxime is its strong tendency to crystallize from solvents as a solvate. The solvate form, however, is not very suitable for pharmaceutical applications. The solvent binding to the substance is very secure and is dissolved only at elevated temperatures. The oxime solvates completely cleave the solvent in general only above 100° C. In this case, depending on the heating rate, inhomogeneous amorphous-crystalline mixed forms are produced.

The purification of the oxime from by-products of the oximization reaction (dioximes, Z-oxime) is carried out by expensive column chromatography with toluene/acetone gradients. A purification by a crystallization process is hampered by the generally poor solubilities in the solvents that are suitable in this respect. A limiting factor is the fact that an isomerization of the E-isomer of the compound into Z-isomer occurs at elevated temperatures in solution.

The object of the invention is therefore to replace the expensive column chromatography by a suitable process and to provide a homogeneous, solvent-free and stable solid form with good pharmaceutical properties.

Figure 1A:
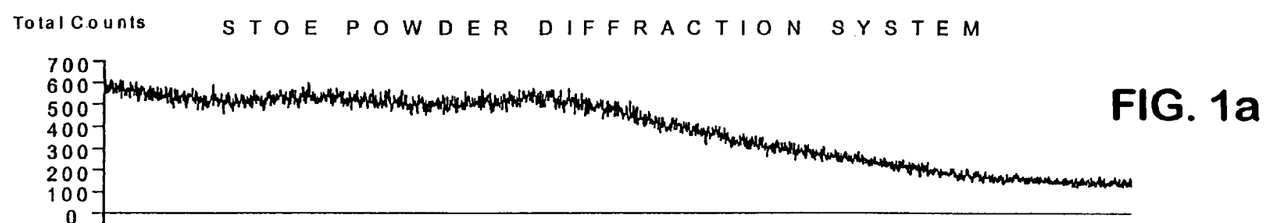
In FIGS. 1a to c, the x-ray-powder diffractogram of amorphous 11β-[4E-(hydroxyiminomethyl)phenyl]-17α-methoxymethyl-17β-methoxy-estra-4,9-dien-3-one or highly crystalline 11β-[4E-(hydroxyiminomethyl)phenyl]-17α-methdxymethyl-17β-methoxy-estra-4,9-dien-3-one ansolvate (cf. Table 1) are depicted.
Figure 1B:
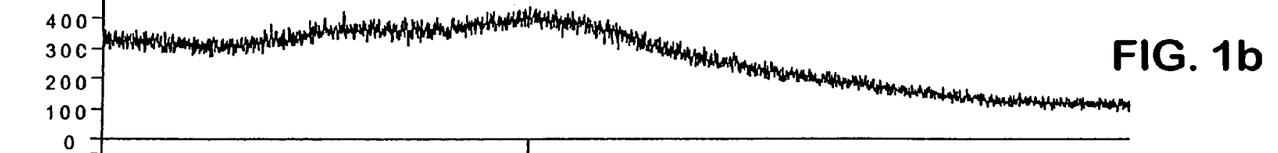
Figure 2:
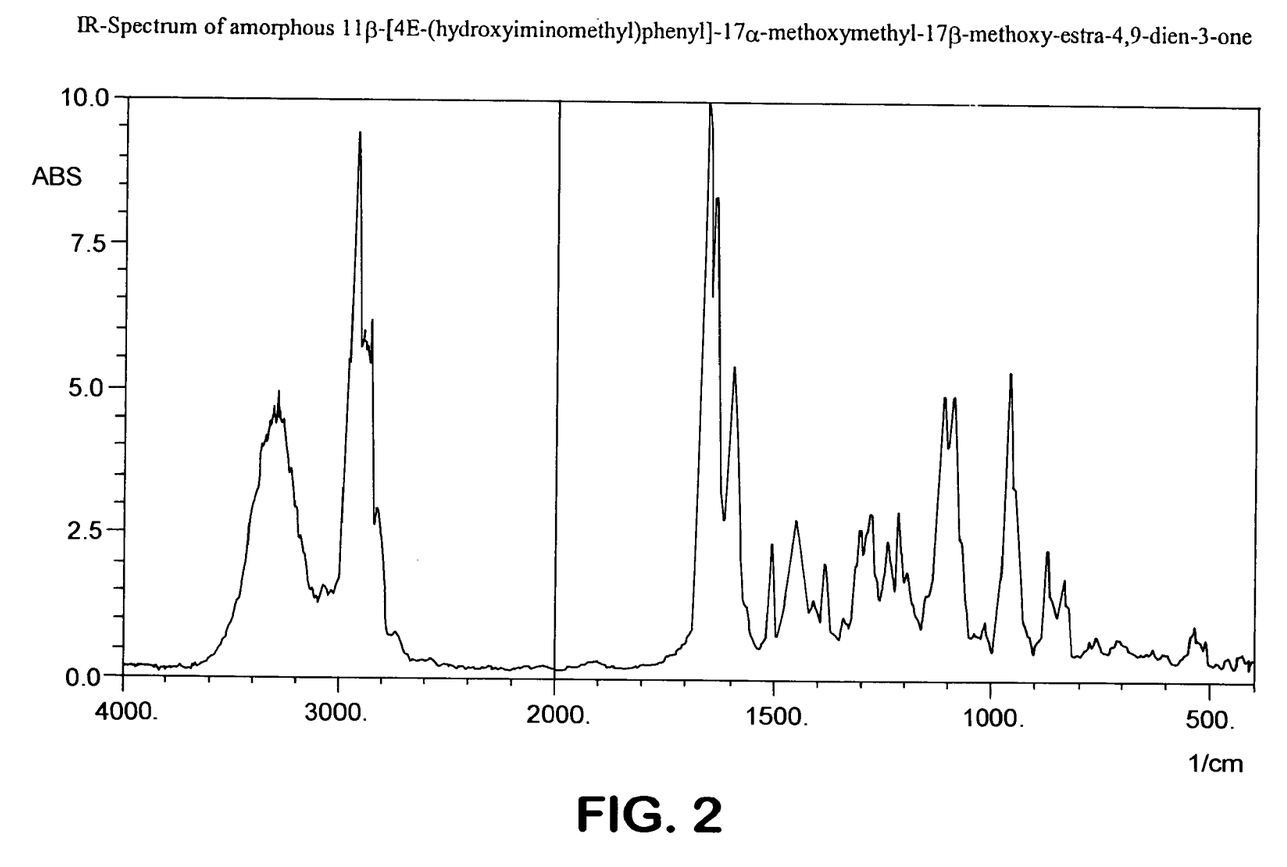
In FIGS. 2 and 3, IR-spectra of amorphous 11β-[4E-(hydroxyiminomethyl)phenyl]-17α-methoxymethyl-17β-methoxy-estra-4,9-dien-3-one or highly crystalline 11β-[4E-(hydroxyiminomethyl)phenyl]-17α-methoxymethyl-17β-methoxy-estra-4,9-dien-3-one ansolvate are depicted.

This object is achieved by amorphous 11β-[4E-(hydroxyiminomethyl)phenyl]-17α-methoxymethyl-17β-methoxy-estra-4,9-dien-3-one, which is characterized in that no crystalline reflexes can be seen in the x-ray-powder diffractogram (XRPD; FIGS. 1a/b) or its modification is characterized by the IR spectrum that is depicted in FIG. 2.

Figure 1C:
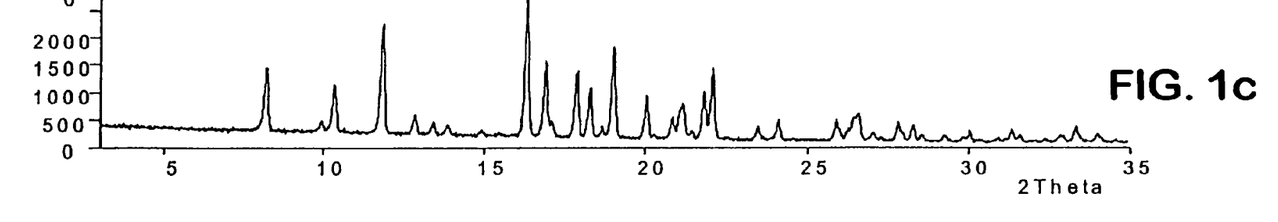
Figure 3:
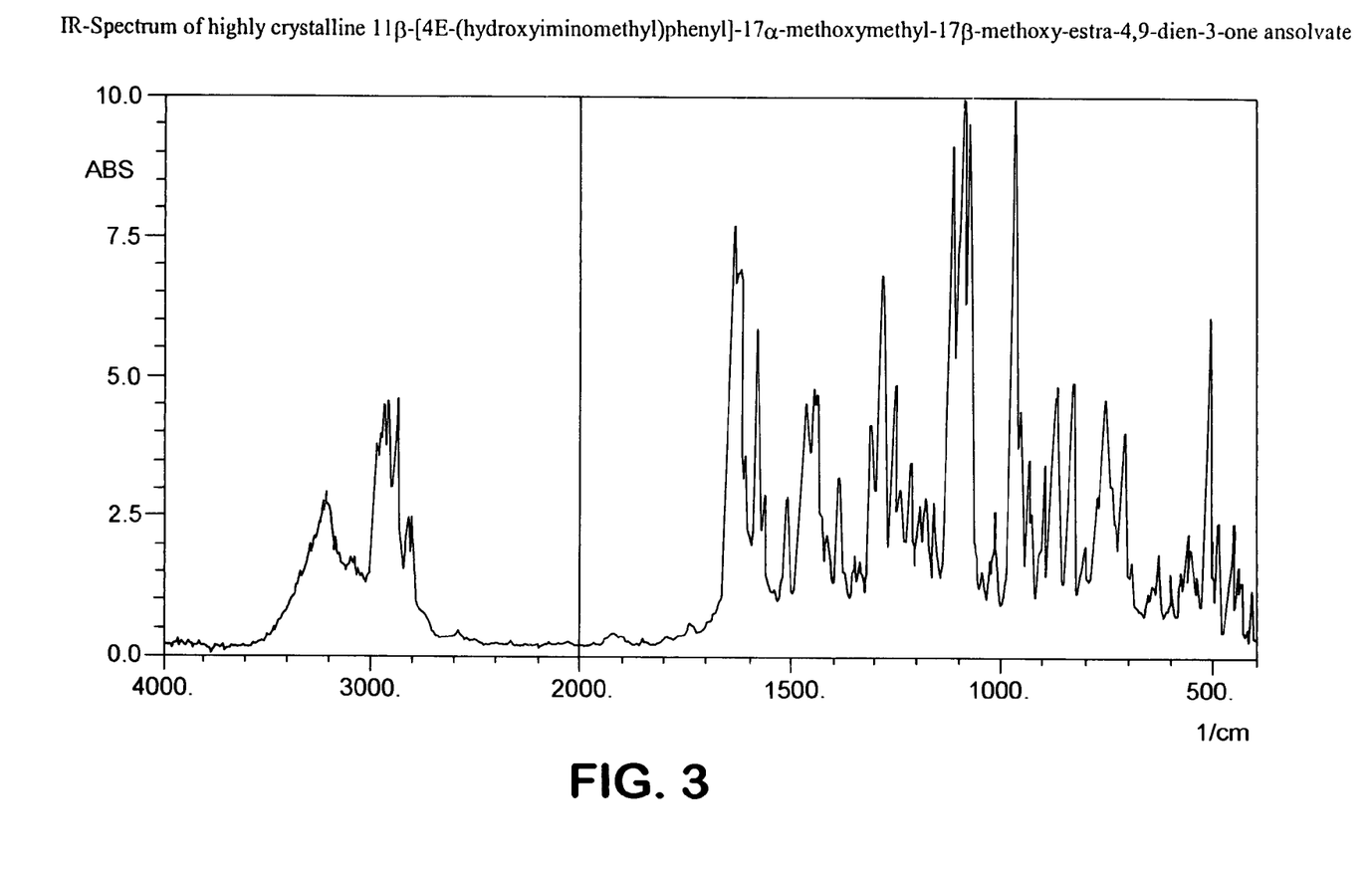

In addition, this object is achieved by highly crystalline 11β-[4E-(hydroxyiminomethyl)phenyl]-17α-methoxymethyl-17β-methoxy-estra-4,9-dien-3-one ansolvate. The crystal form of the ansolvate is characterized by the x-ray-powder diffractogram that is depicted in FIG. 1c or by the IR-spectrum that is depicted in FIG. 3.

Crystalline solvates of 11β-[4E-(hydroxyiminomethyl) phenyl]17α-methoxymethyl-17β-methoxy-estra-4,9-dien-3-one can be produced by a process that comprises the following steps:

a) Production of a solvate of 11β-[4E-(hydroxyiminomethyl)phenyl]-17α-methoxymethyl-17β-methoxy-estra-4,9-dien-3-one and dissolving of the solvate above the saturation solubility in a solvent, especially toluene, which is different from the solvate-solvent and in which the solvate-crystal structure is unstable, b) The optional addition of another solvent as a recrystallization inhibitor, especially methanol or ethyl acetate, and c) The addition of a solvating agent-solvent, especially ethanol, acetone and methyl-tert-butyl ether (MtBE) and crystallization of the solvate.

Figure 4A:
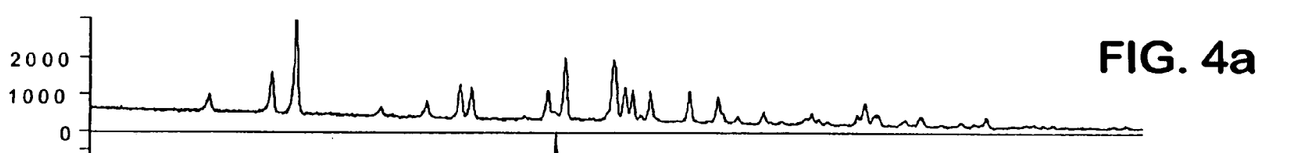
In FIG. 4 (Table 2), x-ray-powder diffractograms of the methyl-tert-butyl ether solvate, the acetone solvate, the ethanol solvate and the isopropanol solvate (cf. Table 2) from 11β-[4E-(hydroxyiminomethyl)phenyl]-17α-methoxymethyl-17β-methoxy-estra-4,9-dien-3-one are depicted.
Figures 4B, 4C:
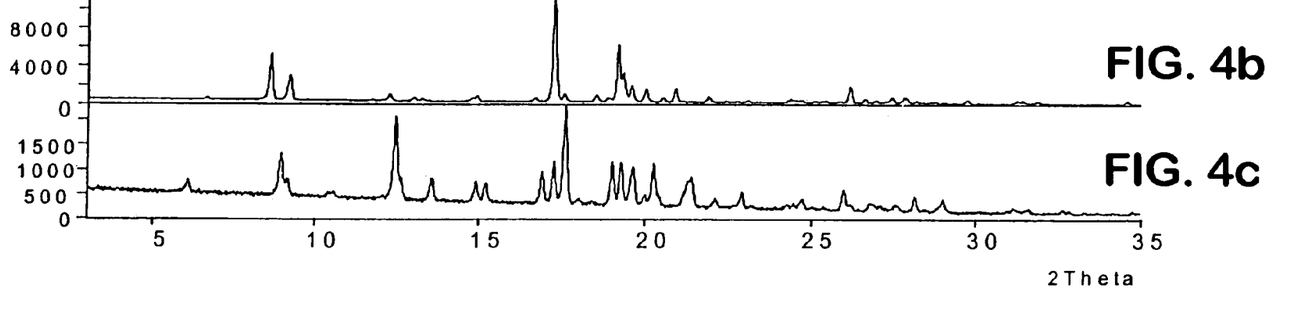
Figure 4D:
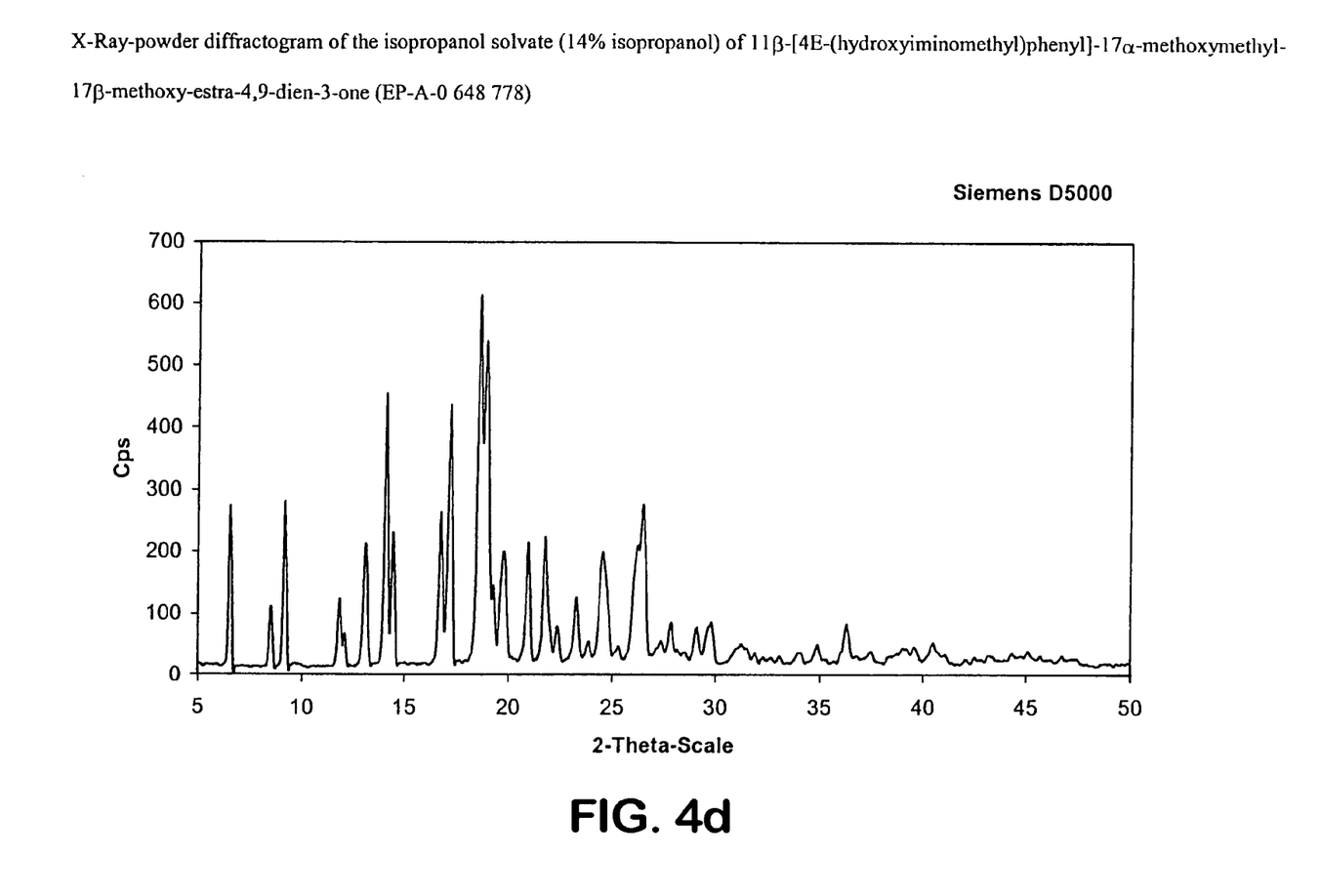

The crystalline solvates of 11β-[4E-(hydroxyiminomethyl)phenyl]-17α-methoxymethyl-17β-methoxy-estra4,9-dien-3-one, namely the methyl-tert-butyl ether solvate, the acetone solvate and the ethanol solvate, whereby the highly crystalline forms are characterized by the x-ray-powder diffractograms depicted in FIGS. 4a/b/c and Table 2, are new and represent intermediate stages toward amorphous 11β-[4E-(hydroxyiminomethyl)phenyl]-17α-methoxymethyl-17β-methoxy-estra-4,9-dien-3-one or toward highly crystalline 11β-[4E-(hydroxyiminomethyl)phenyl]-17α-methoxymethyl-17β-methoxy-estra-4,9-dien-3-one ansolvate.

By drying the crystalline solvates of 11β-[4E-(hydroxyiminomethyl)phenyl]-17α-methoxymethyl-17β-methoxy-estra-4,9-dien-3-one that are obtained above, especially by thermal desolvation preferably under vacuum and at a heating rate in the product of at least 0.5° C./minute or from a solution of the solvate by spray-drying (XRPD; FIG. 1) below the glass transition point of the amorphous structure, the amorphous form of 11β-[4E-(hydroxyiminomethyl)phenyl]-17α-methoxymethyl-17β-methoxy-estra-4,9-dien-3-one is then obtained. The highly crystalline form of 11β-[4E-(hydroxyiminomethyl)phenyl]-17α-methoxymethyl-17β-methoxy-estra-4,9-dien-3-one can be produced by heating the solvate form or the amorphous solid form, optionally in aqueous suspension.

Subjects of this invention are also pharmaceutical compositions, especially solid pharmaceutical compositions, that comprise the above-described amorphous and/or highly crystalline 11β-[4E-(hydroxyiminomethyl)phenyl]-17α-methoxymethyl-17β-methoxy-estra-4,9-dien-3-one in combination with a pharmaceutically compatible vehicle and/or diluent.

The pharmaceutical compositions of this invention are produced with the commonly used solid or liquid vehicles or diluents and the commonly used pharmaceutically technical adjuvants that correspond to the desired type of administration with a suitable dosage in a way that is known in the art.

The term "highly crystalline" according to the invention defines a state from which no further measurable increase of crystallinity (XRPD, DSC) can be determined by conditions that promote the recrystallization of the amorphous structure, such as, e.g., prolonged boiling of the suspended substance in water. The highly crystalline state is characterized in that no exothermic recrystallization peak can be detected between 110° C. and 160° C. in the DSC at a slower heating rate (1K/minute). Only the endothermic melting peak exists at 194.7° C.±2K (heating rate 5K/minute).

TABLE 1

XRPD Data of Highly Crystalline Oxime J867 - d-values ($d_{obs}$), relative intensities ($I_{obs}$) and hkl values of the highest peaks

| $d_{obs}$ [Å] | $I_{obs}$ | h k l |
|---|---|---|
| 10.73 | 40.0 | 1 1 0 |
| 8.88 | 7.6 | 1 0 1 |
| 8.53 | 33.9 | 2 0 0 |
| 7.46 | 80.5 | 1 1 1 |
| 6.88 | 11.7 | 0 2 0 |
| 6.59 | 8.1 | 2 0 1 |
| 6.38 | 6.8 | 1 2 0 |
| 5.95 | 3.4 | 2 1 1 |
| 5.44 | 100.0 | 1 2 1 |
| 5.26 | 55.2 | 3 1 0 |
| 5.20 | 11.3 | 0 0 2 |
| 4.97 | 47.1 | 1 0 2 |
| 4.86 | 36.5 | 0 1 2 |
| 4.76 | 5.9 | 2 2 1 |
| 4.68 | 65.9 | 1 1 2 |
| 4.44 | 27.4 | 2 0 2*<br>1 3 0 |
| 4.27 | 12.9 | 4 0 0 |
| 4.15 | 6.1 | 0 2 2 |
| 4.08 | 30.5 | 1 1 1 3 1*<br>4 1 0 |
| 4.03 | 47.0 | 1 2 2 |
| 3.79 | 8.8 | 4 1 1 |
| 3.70 | 13.0 | 3 1 2 |
| 3.44 | 12.2 | 0 3 2 |
| 3.36 | 18.8 | 0 1 3 |
| 3.30 | 5.9 | 4 0 2 |
| 3.21 | 10.9 | 4 1 2 |
| 3.16 | 11.8 | 5 1 1 |
| 3.13 | 4.7 | 4 3 0 |
| 3.05 | 4.6 | 2 4 1 |
| 2.97 | 5.8 | 4 2 2 |
| 2.89 | 2.9 | 3 1 3 |
| 2.85 | 7.6 | 5 0 2 |
| 2.83 | 4.1 | 1 4 2 |
| 2.69 | 9.7 | 4 0 3*<br>6 1 1 |

*Both hkl values are possible, since the peak separation is limited to 2Θ = 0.08° (angular resolution of the detector).

TABLE 2

XRPD Data of the Solvates of Oxime J867 - d-values ($d_{obs}$) and relative intensities ($I_{obs}$) of the highest peaks

| Ethanol Solvate | | Methyl tert-butyl ether-Solvate | | Acetone Solvate | | Isopropanol Solvate | |
|---|---|---|---|---|---|---|---|
| $d_{obs}$ [Å] | $I_{obs}$ | $d_{obs}$ [Å] | $I_{obs}$ | $d_{obs}$ [Å] | $I_{obs}$ | $d_{obs}$ [Å] | $I_{obs}$ |
| 13.22 | 19.3 | 14.47 | 13.7 | 10.24 | 42.1 | 13.42 | 52.1 |
| 10.27 | 44.4 | 9.86 | 43.9 | 9.58 | 22.8 | 10.34 | 17.8 |
| 9.44 | 100.0 | 9.67 | 18.3 | 7.21 | 5.9 | 9.61 | 51.3 |
| 7.39 | 8.9 | 8.36 | 6.6 | 6.81 | 3.3 | 7.48 | 21.4 |
| 6.64 | 16.6 | 7.10 | 81.7 | 6.68 | 2.0 | 7.33 | 15.6 |
| 6.17 | 39.6 | 6.53 | 22.6 | 5.99 | 3.2 | 6.76 | 36.4 |
| 6.03 | 34.4 | 5.94 | 20.5 | 5.94 | 5.0 | 6.28 | 80.2 |
| 5.21 | 35.6 | 5.82 | 19.5 | 5.32 | 3.2 | 6.13 | 45 |
| 5.06 | 68.7 | 5.24 | 32.3 | 5.14 | 100.0 | 5.29 | 51.6 |
| 4.67 | 72.3 | 5.14 | 42.5 | 5.05 | 6.8 | 5.14 | 69,1 |
| 4.59 | 40.8 | 5.04 | 100.0 | 4.79 | 5.8 | 4.77 | 100.0 |
| 4.54 | 30.3 | 4.92 | 5.6 | 4.70 | 3.3 | 4.69 | 94.4 |
| 4.48 | 6.3 | 4.67 | 42.9 | 4.63 | 51.7 | 4.60 | 22.1 |
| 4.42 | 30.0 | 4.60 | 42.6 | 4.59 | 26.0 | 4.49 | 31.5 |
| 4.17 | 33.5 | 4.52 | 38.5 | 4.53 | 14.3 | 4.23 | 39.7 |
| 4.02 | 25.8 | 4.44 | 9.7 | 4.44 | 11.3 | 4.08 | 38.3 |
| 3.91 | 6.9 | 4.38 | 1.7 | 4.32 | 3.6 | 3.97 | 14.9 |
| 3.78 | 12.5 | 4.16 | 28.8 | 4.25 | 12.6 | 3.82 | 23.8 |
| 3.70 | 4.5 | 4.02 | 9.2 | 4.06 | 4.7 | 3.73 | 11.6 |
| 3.59 | 7.8 | 3.88 | 15.9 | 3.65 | 2.7 | 3.62 | 37.1 |
| 3.57 | 13.3 | 3.66 | 5.0 | 3.63 | 2.1 | 3.59 | 22.4 |
| 3.54 | 7.0 | 3.63 | 5.4 | 3.40 | 14.6 | 3.41 | 35.0 |
| 3.50 | 4.2 | 3.59 | 9.6 | 3.34 | 3.5 | 3.39 | 35.9 |
| 3.38 | 10.0 | 3.42 | 20.5 | 3.30 | 2.1 | 3.36 | 37.61 |
| 3.35 | 23.9 | 3.32 | 7.8 | 3.25 | 4.8 | 3.26 | 11.8 |
| 3.32 | 12.5 | 3.29 | 5.5 | 3.20 | 5.0 | 3.2 | 14.0 |
| 3.30 | 12.7 | 3.23 | 6.4 | 3.16 | 2.0 | 3.07 | 16.4 |
| 3.21 | 6.3 | 3.17 | 14.5 | 3.00 | 3.4 | 3 | 13.6 |
| 3.15 | 10.7 | 3.07 | 12.2 | 2.86 | 2.1 | 2.47 | 12.65 |
| 3.02 | 4.9 | 2.87 | 5.6 | 2.85 | 2.2 | 2.23 | 10.6 |
| 2.98 | 3.7 | 2.83 | 4.6 | 2.81 | 2.2 | | |
| 2.95 | 10.6 | | | 2.59 | 2.4 | | |

The invention relates to a new highly pure and stable, amorphous or highly crystalline form of the mesoprogestin 11β-[4E-(hydroxyiminomethyl)phenyl]-17α-methoxymethyl-17β-methoxy-estra-4,9-dien-3-one (J 867):

and solvate forms of J867, which represent intermediate products for the production of the amorphous or highly crystalline form. It has proven to be a problem in the production of the amorphous or highly crystalline form that in the stage of desolvation, the substance passes through an amorphous intermediate stage, from which the ansolvate/anhydrate form recrystallizes more or less completely depending on the heating rate, final temperature and drying period. The degree of crystallinity, however, is difficult to control, so that inhomogeneous mixed forms that consist of amorphous and crystalline portions are produced. In addition, the thermal stress of the chemical structure that tends toward Z-isomerization and oxime-cleavage results in a deterioration of purity.

The production of the solvate form that is suitable for the solid final form of the oxime can be associated, according to the invention, with the separation of the Z-isomer and the dioximes. By a specific use of the thermodynamic instability of suitable solvates, preferably the solvate of methyl-tert-butyl ether (MTBE) in a solvent environment that is suitable for this purpose, complete dissolution of the solvate lattice is possible far above the solubility limit and even close to room temperature. In contact with toluene in a mass ratio of 1:2 to 1:1, the crystal form of the MTBE solvate dissolves quickly and completely, despite the only slight solubility in toluene of only 3.3% by weight, even at 20-35° C. A so-called cold melting is carried out. This state can be kept stable by adding suitable solvents as recrystallization inhibitors for technical applications. The supersaturation state can be stabilized for hours in toluene solution by adding only 5% by volume of methanol. Then, by adding solvating agent-solvent (MTBE) at suitable concentration (e.g., 100-130% by volume of MTBE, relative to the toluene that is used), the solvate lattice is built up again, whereby the contaminants remain in solution for the most part.

By an especially quick drying process, preferably spray-drying, below the glass transition point directly from the solution of oxime solvate J867 in an organic solvent, preferably ethanol, a stable, completely amorphous, solvent-free structure can be obtained. To this end, oxime that is dissolved in ethanol to a level of 3 to 13% by weight is sprayed using a suitable spraying unit (binary nozzle or centrifugal sprayer) in hot nitrogen and is dried in an extremely short time to form amorphous, microfine particles. The starting temperature of the nitrogen in this case is 120° C. to 200° C., preferably 150° C.-180° C. The ratio of oxime solution to drying gas in this case should be 0.01 to 0.3 kg of solution/m$^3$ of N$_2$, preferably 0.08 to 0.12 kg of solution/m$^3$ of N$_2$. The drying process is controlled such that in the dryer outlet, a temperature of 55° C. to 95° C., preferably 75 to 85° C., is set. This temperature is significantly below the glass transition temperature of the amorphous oxime (105° C.), where the substance assumes a gel/glass-like consistency and above which a more or less quick or spontaneous recrystallization can take place.

By applying spray-drying, a solvent-free, homogeneous or microfine solid form of oxime J 867 is obtained in one process step.

Figure 5A:
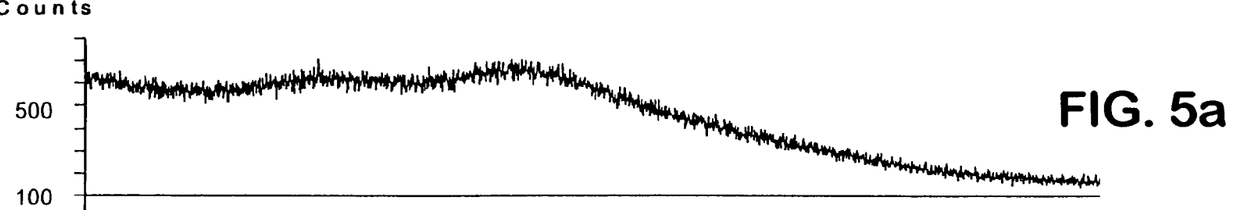
In FIG. 5, an x-ray-powder diffractogram of amorphous 11β-[4E-(hydroxyiminomethyl)phenyl]-17α-methoxymethyl-17β-methoxy-estra-4,9-dien-3-one is depicted at time 0 (start), after 12 months at 25° C. and after 12 months at 40° C.
Figure 5B:
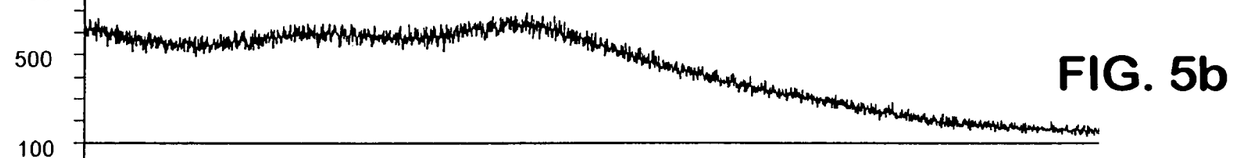
Figure 5C:
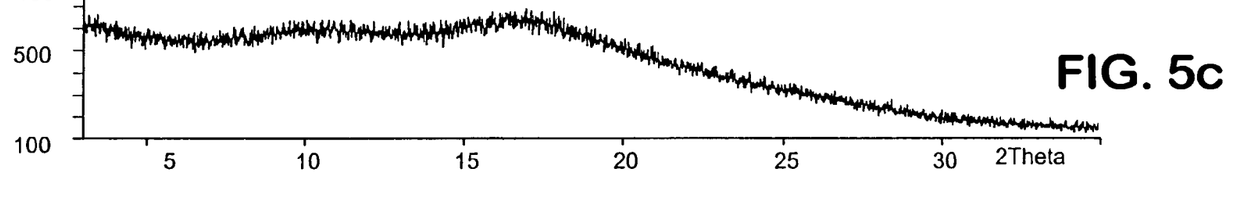

The advantage of using the amorphous form of oxime J867 according to the invention for the production of pharmaceutical agents lies in the fact that in addition to the good solubility properties, this amorphous structure, surprisingly enough, has a very good shelf life. Also, after 12 months in the accelerated ICH-stability test (40° C., 75% relative humidity), the amorphous structure does not show any signs of a recrystallization and/or chemical decomposition (see FIG. 5). Also, during the pharmaceutical processing (wet granulation, pelletizing), the physical structure of the oxime remains stable. This means that a conversion of the amorphous into the highly crystalline form or an E/Z isomerization does not occur. By the stability, negative influences of such conversions on the bio-availability of the active ingredient are avoided.

Relative to the shelf life, the same correspondingly holds true for the use of the highly crystalline form of oxime J 867 according to the invention, whereby as expected, the chemical stability, especially under stress (high temperatures and humidities) is higher than that of the amorphous form.

Figure 6A:
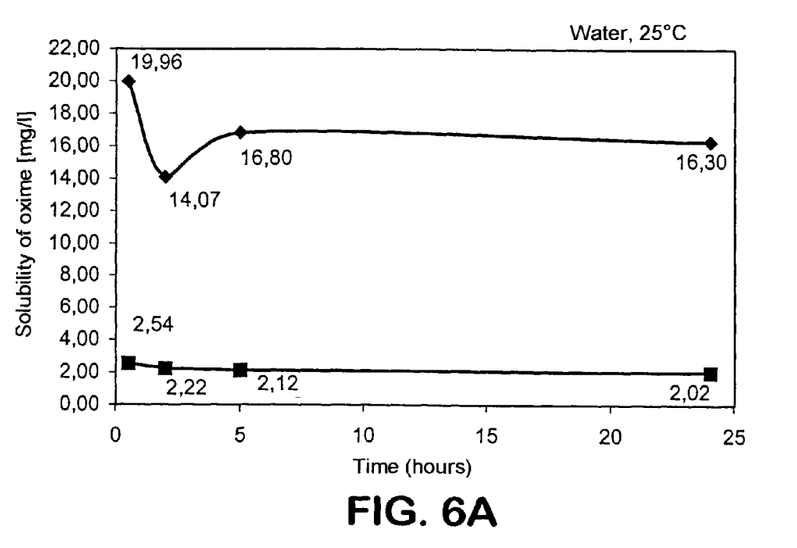
In FIG. 6, the solubility of highly crystalline 11β-[4E-(hydroxyiminomethyl)phenyl]-17α-methoxymethyl-17β-methoxy-estra-4,9-dien-3-one ansolvate or amorphous 11β-[4E-(hydroxyiminomethyl)phenyl]-17α-methoxymethyl-17β-methoxy-estra-4,9-dien-3-one in water is shown with and without surfactant.
Figure 6B:
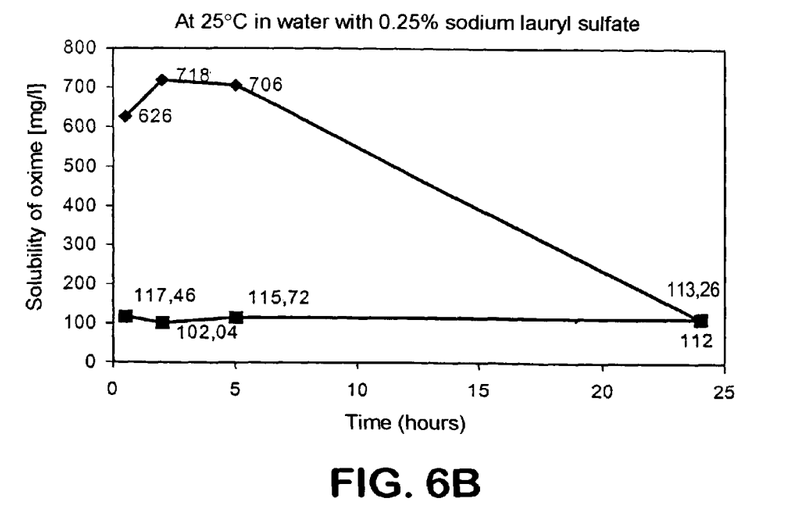

In addition, the amorphous form has excellent solubility properties. The saturation solubility in water and in the surfactant solution (025% sodium lauryl sulfate) is approximately 7 to 8× higher than that of the highly crystalline form, whereby this high supersaturation level remains stable for several hours, as in the case of water for over 24 hours (see FIG. 6).

The production of the highly crystalline form can be carried out starting from one of the solvate forms of oxime J867. In this respect, the solvate form can be suspended in water at a temperature of from 50 to 100° C.; in this case, the solvent is cleaved far below the desolvation temperature of the dry solvate form. In the case of the MTBE solvate, an only short-term treatment (10 to 30 minutes) with water at a temperature of 65 to 75° C. for complete conversion into the highly crystalline form already results.

With the process according to the invention, especially the thermal desolvation, it is basically possible, depending on the process conditions, to produce amorphous-crystalline mixed forms that can pose considerable problems that cannot be reproduced, but can hinder the development of a validated production process for quality control, further pharmaceutical processing and official approval.

Oxime J867 is a substance that has an antigestagenic action according to EP-A-0 648 778 or DE-A-43 32 283 and that with the same activity as RU 486 (mifepristone) on the progesterone receptor has an antiglucocorticoidal activity that is significantly reduced in comparison to RU 8486.

In U.S. application Ser. Nos. 09/386,141, 09/386,140 and 09/386,133, oxime J 867 is referred to as mesoprogestin. In this connection, mesoprogestins are defined as compounds that have in vivo both agonistic and antagonistic activity on the progesterone receptor (PR). Corresponding functional conditions cannot be achieved with gestagen and antigestagen.

Oxime J 867 is suitable in particular for the following uses:
a) Oxime J 867 can be used according to U.S. application Ser. No. 09/386,133, optionally together with an estrogen, for the production of a pharmaceutical agent for female contraception.
b) Oxime J 867 can be used according to U.S. application Ser. No. 09/386,141 for treating and preventing benign hormone-dependent gynecological disorders; such as
   for treating gynecological disorders, such as endometriosis, uterine fibroids, post-operative peritoneal adhesions, dysfunctional bleeding (metrorrhagia, menorrhagia) and dysmenorrhea;
   for preventing gynecological disorders; such as postoperative, peritoneal adhesions, dysfunctional uterine bleeding (metrorrhagia, menorrhagia) and dysmenorrhea. The daily dose of the mesoprogestin is 0.5 to 100 mg, preferably 5.0 to 50 mg and a maximum of preferably 10 to 25 mg.
c) Oxime J867 according to U.S. application Ser. No. 09/386,140 can also be used as a pharmaceutical component for the production of a pharmaceutical agent optionally together with an estrogen in hormone replacement therapy (HRT) and for treating hormone deficiency and symptoms of hormonal irregularity.

Measuring Process

X-Ray-Powder Diffractometry (X-Ray Powder Diffraction: XRPD):

The data were determined with an STOE powder diffractometer STADIP with germanium-monochromatic CuK$_{\alpha 1}$ radiation ($\lambda$=1.540598 Å)—between $3° \leqq 2\Theta \leqq 35°$ or a Siemens diffractometer D5000 with a Cu-anode ($5° \leqq 2\Theta \leqq 50°$).

IR Spectroscopy:

A NICOLET 20 SXB with a photoacoustic detector MTEC (KBr, 8t, 90 seconds) was used.

Solubility Studies:

200 mg of substance was added at 25° C. into 50 ml of water (without and with 0.25% SDS (sodium lauryl sulfate)). Samples were taken after 0.5 hour, 2 hours, 5 hours and 24 hours.

Sampling: 0.45 μm filter attachment, dilution 1:1 with MeOH, HPLC.

HPLC

The determination of purity is carried out according to the following method:
Column: Superspher Si 60, 250×4 mm, 4 μm
Eluant: Chloroform (3% ethanol)/water such as 96.9/0.1
Flow: 1 ml/minute
Detection: UV (299 nm)
Evaluation: 100% surface normalization Headspace for Residual Solvent:
GC-Auto system with HS40 Perkin Elmer, DB-Wax column, 30 m×0.23 mm, FID.

Grain Size Distribution:
Sympatec HELOS (H0445), dry dispersing system (RODOS), pressure 2 bar.

DSC:
Perkin Elmer DSC 7 and NETZSCH DSC 200/1/F in Pan-Al, pierced lid, nitrogen.

The invention is explained in more detail by the examples that now follow.

EXAMPLES

Example 1

2 kg of oxime J867 (MtBE solvate with 20 to 24% MtBE; unless otherwise indicated, the percent of solvent contained in the solvates is % by weight) is dissolved in 20 l of ethanol, at 50° C. while being stirred. The solution is spray-dried in a co-current process in a spray-dryer that is operated under inert conditions (nitrogen). The drying chamber of the spray dryer is coated with 60 m³/h of nitrogen, which is preheated to 175° C. Then, the solution is sprayed into the drying chamber via a flow inducer with 6.4 l/h with a binary nozzle that is operated with 3 bar of nitrogen as a propellant. The drying gas outlet temperature is 79° C.-83° C. The oxime J867 that is dried into microfine particles is completely collected in a product filter.

Oxime J867 has the following quality parameters:

| | |
|---|---|
| Residual Solvent | 0.44% Ethanol, 0.11% MtBE |
| Water | 0.5% |
| Grain Size | 100% < 12.5 μm |
| | 50% < 2.25 μm |
| | 10% < 0.82 μm |
| Purity | No Z-isomerization during the thermal stress: 1.7 F % |
| (Content of | (percent by surface area) before drying |
| Z-Oxime) | 1.7 F % after drying |
| XRPD | 100% amorphous - no crystalline reflexes |

Example 2

50 ml of toluene is added to 20 g of oxime J867 (MTBE solvate with 20%-24% MtBE). The substance dissolves very quickly and completely at 25° C. 2.7 ml of methanol is added to the solution, and the solution is then mixed with 65 ml of MtBE. After about 1 minute, the recrystallization of the MtBE solvate begins. The entire process is carried out at room temperature. The suspension is stirred for 1 hour at 5° C., then filtered, and the filter cake is washed with 30 ml of cold MtBE. After drying, the yield is 84% by weight of the charging material. The product that is obtained is in turn an MTBE solvate with 22.3% MTBE. The purification effect relative to the main contaminants can be seen in the table below:

| | Charging Material | Recristallizate |
|---|---|---|
| E-Oxime | 97.7 F % | 98.8 F % |
| Z-Oxime | 1.7 F % | 1.0 F % |
| Dioxime | 0.4 F % | 0.04 F % |

Example 3

30 g of MtBE solvate of oxime J867 (MtBE solvate with 20 to 24% MtBE) is suspended in 600 ml water and heated to 70° C. and suspended for 30 minutes. The suspension is filtered and suctioned off in the dry state in a stream of air. Then, the crystallizate is dried in a vacuum for 3 hours at 70° C. and <5 mbar.

24 g of highly crystalline oxime J867 is obtained.

The phase conversion in hot water and the drying do not result in any significant increase of the Z-isomer and the aldehyde.

| | Z-Oxime (HPLC) | Aldehyde (HPLC) |
|---|---|---|
| MTBE Solvate of Oxime J867 | 1.58 F % | 0.17 F % |
| Highly Crystalline Ansolvate of Oxime J867 | 1.61 F % | 0.13 F % |

In XRPD, with respect to the intensity and the locations of the reflexes and in the DSC with respect to the melting heat, a similarity to the data of the highly crystalline ansolvate form of oxime J867 was detected.

The invention claimed is:

1. Amorphous 11β-[4E-(hydroxyiminomethyl)phenyl]-17α-methoxymethyl-17β-methoxy-estra-4,9-dien-3-one, substantially separate from its corresponding Z-isomer.

2. Amorphous 11β-[4E-(hydroxyiminomethyl)phenyl]-17α-methoxymethyl-17β-methoxy-estra-4,9-dien-3-one according to claim 1, which is substantially solvent-free.

3. Amorphous 11β-[4E-(hydroxyiminomethyl)phenyl]-17α-methoxymethyl-17β-methoxy-estra-4,9-dien-3-one of claim 1 in substantially pure form.

4. Amorphous 11β-[4E-(hydroxyiminomethyl)phenyl]-17α-methoxymethyl-17β-methoxy-estra-4,9-dien-3-one of claim 1, which contains no more than about 1.7% weight of the corresponding Z-isomer.

5. Pharmaceutical composition that comprises amorphous 11β-[4E-(hydroxyiminomethyl)phenyl]-17α-methoxymethyl-17β-methoxy-estra-4,9-dien-3-one according to claim 1, in combination with a pharmaceutically compatible vehicle and/or diluent.

6. A method for female birth control, for treating a hormone-dependent gynecological disorder or for hormone replacement therapy, which comprises administering to a patient an amorphous 11β-[4E-(hydroxyiminomethyl)phenyl]-17α-methoxymethyl-17β-methoxy-estra-4,9-dien-3-one according to claim 1.

7. Amorphous 11β-[4E-(hydroxyiminomethyl)phenyl]-17α-methoxymethyl-17β-methoxy-estra-4,9-dien-3-one, substantially separate from its corresponding Z-isomer, obtained by drying of a crystalline solvate of 11β-[4E-(hydroxyiminomethyl)phenyl]-17α-methoxymethyl-17β-methoxy-estra-4,9-dien-3-one below the glass transition point of the amorphous substance, whereby the drying of the solvate is carried out during the desolvation phase with a heating rate in the product of at least 0.5° C./minute or from a solution of the solvate by spray-drying.

8. Amorphous 11β-[4E-(hydroxyiminomethyl)phenyl]-17α-methoxymethyl-17β-methoxy-estra-4,9-dien-3-one of claim 7 in substantially pure form.

9. Amorphous 11β-[4E-(hydroxyiminomethyl)phenyl]-17α-methoxymethyl-17β-methoxy-estra-4,9-dien-3-one of claim 7, which contains no more than about 1.7% weight of the corresponding Z-isomer.

10. A crystalline solvate of 11β-[4E-(hydroxyiminomethyl)phenyl]-17α-methoxymethyl-17β-methoxy-estra-4,9-dien-3-one, substantially separate from its corresponding Z-isomer, selected from: the methyl-tert-butyl ether solvate, whereby the crystalline form is characterized by the x-ray-powder diffractogram that is depicted in FIG. 4c (Table 2); and the ethanol solvate, whereby the crystalline form is characterized by the x-ray-powder diffractogram that is depicted in FIG. 4a (Table 2).

11. A crystalline solvate of 11β-[4E-(hydroxyiminomethyl)phenyl]-17α-methoxymethyl-17β-methoxy-estra-4,9-dien-3-one according to claim 10 in substantially pure form.

12. A crystalline solvate of 11β-[4E-(hydroxyiminomethyl)phenyl]-17α-methoxymethyl-17β-methoxy-estra-4,9-dien-3-one according to claim 10, which contains no more than about 1.7% weight of the corresponding Z-isomer.

13. Process for the production of amorphous 11β-[4E-(hydroxyiminomethyl)phenyl]-17α-methoxymethyl-17β-methoxy-estra-4,9-dien-3-one that comprises the drying of a crystalline solvate of 11β-[4E-(hydroxyiminomethyl)phenyl]-17α-methoxymethyl-17β-methoxy-estra-4,9-dien-3-one, according to claim 10, below the glass transition point of the amorphous substance, whereby the drying of the solvate is carried out during the desolvation phase with a heating rate in the product of at least 0.5° C./minute or from a solution of the solvate by spray-drying.

14. Process for the production of a crystalline solvate of 11β-[4E-(hydroxyiminomethyl)phenyl]-17α-methoxymethyl-17β-methoxy-estra-4,9-dien-3-one according to claim 10 that comprises the following steps:

a) production of a solvate of 11β-[4E-(hydroxyiminomethyl)phenyl]-17α-methoxymethyl-17β-methoxy-estra-4,9-dien-3-one and dissolution of the solvate above the saturation solubility in a solvent that is different from the solvate solvent and in which the solvate-crystal structure is unstable, b) the optional addition of another solvent as a recrystallization inhibitor, and c) the addition of a solvating agent-solvent and crystallization of the solvate.

* * * * *